US006797516B1

(12) United States Patent
Chen et al.

(10) Patent No.: US 6,797,516 B1
(45) Date of Patent: Sep. 28, 2004

(54) MASS SPECTROMETRIC SCREENING OF CATALYSTS

(75) Inventors: Peter Chen, Zurich (CH); Christian Hinderling, Zurich (CH)

(73) Assignee: Thales Technologies AG, Zurich (CH)

(*) Notice: Subject to any disclaimer, the term of this patent is extended or adjusted under 35 U.S.C. 154(b) by 0 days.

(21) Appl. No.: 09/489,863

(22) Filed: Jan. 24, 2000

Related U.S. Application Data

(60) Provisional application No. 60/136,416, filed on May 28, 1999, and provisional application No. 60/117,205, filed on Jan. 25, 1999.

(30) Foreign Application Priority Data

Jan. 22, 1999 (CH) ............................................. 125/99
Jun. 21, 1999 (CH) ............................................ 1147/99

(51) Int. Cl.[7] ........................................... G01N 31/10
(52) U.S. Cl. ..................... 436/37; 250/281; 250/282; 250/288; 436/173
(58) Field of Search .......................... 436/37, 85, 161, 436/173; 250/281–282, 288

(56) References Cited

U.S. PATENT DOCUMENTS

| 4,626,412 | A |   | 12/1986 | Ebner et al. ................... 422/50 |
| 5,009,849 | A | * | 4/1991  | Ebner et al. ................... 422/83 |
| 5,222,390 | A | * | 6/1993  | Monrabal .................. 73/61.76 |
| 5,959,297 | A | * | 9/1999  | Weinberg et al. ........... 250/288 |
| 6,063,633 | A | * | 5/2000  | Willson, III ................. 436/37 |

FOREIGN PATENT DOCUMENTS

| EP | 435146 A2 |   | 7/1991 |
| EP | 755938 A1 |   | 1/1997 |
| WO | 98/15969  | * | 4/1998 |

OTHER PUBLICATIONS

J. D. Gargulak et al, *J. Am. Chem. Soc.* 1991, 113, 1054–1055.*
A. J. Canty et al, *Inorg. Chim Acta* 1993, 210, 91–97.*
Azran, J. et al, Journal of Molecular Catalysis 1983, 18, 105–108.*

(List continued on next page.)

*Primary Examiner*—Arlen Soderquist
(74) *Attorney, Agent, or Firm*—Greenlee, Winner and Sullivan, P.C.

(57) ABSTRACT

Screening methods to identify catalysts or to identify improved catalysts using mass spectrometric analysis of products of catalysis, particularly catalyst-bound intermediate products in the catalytic cycle. The methods are applicable, in particular, to screening of organometallic compounds for catalytic function. Moreover, the methods are applicable, in particular, to screening for catalysts for polymerization reactions. More specifically, the methods employ a two stage (or two step) mass spectrometric detection method in which ions formed in a first stage ionization and which are linked to catalyst performance are selected and the catalyst associated with the selected ion is identified in a second stage employing tandem mass spectrometry. In specific embodiments, the screening methods of this invention avoid explicit encoding because the identity of the catalyst is implicitly contained in the product molecular mass (typically an intermediate product), since the catalyst (or a portion thereof) remains attached to the product.

21 Claims, 5 Drawing Sheets

OTHER PUBLICATIONS

Usami, T. et al, Macromolecules 1986, 19, 2722–2726.*
Hussain, S. T. Journal of the Chemical Society of Pakistan 1994, 16, 87–91.*
Smith, M. E. et al, Macromolecules 1994, 27, 2701–2707.*
G. Holzmann et al, Makromol. Chem. 1982, 183, 1711–1731.*
U. Ackelid et al, Vacuum 1991, 42, 889–895.*
K. Soga et al, Polymer 1992, 33, 2408–2411.*
F. Y. Xu et al, Makromol. Chem. 1993, 194, 2579–2603.*
D. R. Maloney et al, J. Chem. Soc., Chem. Commun. 1995, 561–562.*
W. J. Evans et al, Macromolecules 1995, 28, 7929–7936.*
H. Schubert et al, Fresenius' J. Anal. Chem. 1996, 356, 127–137.*
D. M. Haddelton et al, Polymer Preprints: Am. Chem. Soc. Div. Polym. Chem. 1997, 38, 452–453.*
D. Kukuli et al, J. Polym. Sci. A: Polym. Chem. 1997, 35, 859–878.*
J. Wu et al, Chem. Biol. 1997, 4, 653–657.*
V. J. Ruddick et al, J. Phys. CHem. B 1998, 102, 2991–2994.*
Aliprantis, A. O. and Canary, J.W. (1994), "Observation of Catalytic Intermediates in the Suzuki Reaction by Electrospray Mass Spectrometry," J. Am. Chem. Soc. 116:6985–6986.
Boussie et al. (Dec. 1998) "Festphasensynthese und Kodierung von Katalysatoribibliotheken für Olefinpolymerisationen," Angew. Chem. 110:3472–3475.
Britovsek et al. (Feb. 1999), "Auf der Suche nach einer neuen Generation von Katalysatoren zur Olefinpolymerisation:„Leben jenseits der Metallocene," Angew. Chem. 111:448–468.
Brookhart et al. (1992), "Palladium(III) Catalysts for Living Alternating Copolymerization of Olefins and Carbon Monoxide," J. Am. Chem. Soc. 114:5894–5895.
Burgess et al. (1996), "Durch Screening ermittelte Katalysatoren und Reaktionsbedingungen für eine C–H–Insertionrsreaktion," Angew. Chem. 108:192–194.
Cole et al. (1996), "Entwicklung von chiralen Katalysatoren durch kombinatorische Ligandenvariation—Ti–katalysierte enantioselektive Addition von TMSCN and meso–Epoxide," Angew. Chem. 108:1776–1779.
Cooper et al. (1998), "Reactive Dyes as a Method for Rapid Screening of Homogeneous Catalysts," J. Am. Chem. Soc. 120:9971–9972.
Colton, R. and Traeger, J.C. (1992), "The application of electrospray mass spectrometry to ionic inorganic and organometallic systems," Inorg. Chim. Acta 201:153–155.
Colton, et al. (Jun. 1995), "Electrospray Mass Spectrometry Applied to Inorganic and Organometallic Chemistry," Mass Spec. Rev. 14:79–106.
Dieck et al. (1981), "Bis(diazadien)metall (O)–Komplexe, IV[1]Nickel (O)–bis(chelate) mit aromatischen N–Substituenten," Z. Naturforsch. 36b:823–832.
Drent, E. and Budzelaar, P.H.M. (1996), "Palladium–Catalyzed Alternating Copolymerization of Alkenes and Carbon Monoxide," Chem. Rev. 96:663–681.
Dzhabieva et al. (1996), "Electrospray mass spectrometric study of homogeneous catalytic system $Pd(CF_3COO)_2–Ph_2P(CH_2)_3PPh_2–MeOH/Me_2CO–H_2O$ for copolymerization of ethylene and carbon monoxide," Russ. Chem. Bull. 45:474–476.

Feichtinger, D. and Plattner, D.A. (Sep. 1997), "Direkter Nachweis von $Mn^V$–oso–salen–Komplexen," Angew. Chem. 109(16):1796–1798.
Feichtinger et al. (Jul. 1998), "Ziegler–Natta like Olefin Oligomerization by Alkylzirconocene Cations in an Electrospray Ionization Tandem Mass Spectrometer," J. Am. Chem. Soc. 120:7125–7126.
Festage et al. (1998), "Effects of Molecular Entanglements During Electrospray of High Molecular Weight Polymers," J. Am. Soc. Mass Spec. 9:299–304.
Francis, M. B. and Jacobsen, E.N. (Apr. 1999), "Entdeckung neuer Katalysatoren für die Alkenepoxidierung durch metallbindende kombinatorische Bibliotheken," Angew. Chem. 111(7):987–991.
Goodall et al. (1993), "Novel Catalysis for the Ring–Opening Methathesis Polymerization of Norbornene–Type Monomers," J. Appl. Polymer Sci 47:607–617.
Hinderling et al. (1997), "A Combined Gas–Phase, Solution–Phase, and computational Study of C–H Activation by Cationic Iridium (III) Complexes," J. Am. Chem. Soc. 119(44):10793–10804.
Hunt et al. (Mar. 1998), "Probing the Effects of Cone Potential in the Electrospray Ion Source: Consequences for the Determination of Molecular Weight Distributions of Synthetic Polymers," Anal. Chem. 70:1812–1822.
Jackson, C.A. and Simonsick, W. J. (1997), "Application of Mass Spectrometry to the Characteization of Polymers," Curr. Opin, Solid State Mater. Sci. 2:661–667.
Johnson et al. (1995), "New Pd(II)– and Ni(II)–Based Catalysts for Polymerization of Ethylene and a–Olefins," J. Am. Chem. Soc. 117:6414–6415.
Johnson et al. (1996), "Copolymerization of Ethylene and Propylene with Functionalized Vinyl Monomers by Palladium(II) Catalysts," J. Am. Chem. Soc. 118:267–268.
Kane–Maguire et al. (1995), "Comparison of Electrospray Mass Spectrometry with other Soft Ionization Techniqes for the Characterisation of Cationic π–hydrocarbon Organometallic Complexes," J. Organomet. Chem. 486:243–248.
Katta et al. (1990), "Electrospray Ionization: A New Tool for the Analysis of Ionic Transition–Metal Complexes," J. Am. Chem. Soc. 112:5348–5349.
Killian et al. (1997), "Preparation of Linear Alpha–Olefins using Cationic Nickel (II) Alpha–Diimine Catalysts" Organometallics 16:2005–2007.
Kim et al. (1999), "Reactions of Electrosprayed Rhodium Phosphine Complexes in the Gas–Phase: Modeling Homogeneous Catalytic Hydrogenation" Int. J. Mass Spectrom. 185:871–881.
Kliegman, J.M. and Barnes, R.K. (1970), "Glyoxal Derivatives. II. Reaction of Glyoxal with Aromatic Primary Amines," J. Org. Chem. 35(9):31403143.
Lipshutz et al. (1996), "Analyses of Anionic Cu(I) Complexes via Electrospray Mass Spectrometry," J. Am. Chem. Soc. 118:6796–6797.
Lorenz et al. (1999), "Electrospray Ionization Fourier Transform Mass Spectrometry of Macromolecules: The First Decade," Appl. Spect. 53(1):18A–36A.
Margl et al. (1999), "A Unified View of Ethylene Polymerization by $d^0$ and $d^0f^n$ Transition Metals. 3. Termination of the Growing Polymer Chain," J. Am. Chem. Soc. 121:154–162.

McCann et al. (1995), "Single Crystals of Isopolyoxometallate (VI) Salts as Catalysts for the Ring–Opening Polymerization of Norbornene," J. Mol. Catalysis A 96:31–34.

Rulke et al. (1993), "NMR Study on the coordination Behavior of Dissymmetric Terdentate Trinitrogen Ligands on Methylpalladium(II) Compounds," Inorg. Chem. 32:5769–5778.

Saf et al. (1996), "Electrospray Ionization Mass Spectrometry Investigation of Oligomers Prepared by Ring–Opening Metathesis Polymerization of Methyl N–(1–Phenylethyl)–2azabicyclo[2.2.1]hept–5–ene–3–carboxylate," Macromolecules 29:7651–7656.

Senkan, S.M. (Jul. 1998), "High–throughput screening of solid–state catalyst libraries," Nature 394:350–353.

Small et al. (Apr. 1998) "Highly Active Iron and Cobalt Catalysts for the Polymerization of Ethylene," J. Am. Chem. Soc. 120:4049–4050.

Spence et al. (1997), "Controlled Synthesis of Transition–Metal Ion Complex/Solvent Clusters by Electrospray Ionization," J. Phys. Chem. A 101:139–144.

Spence et al. (1997), "Wavelength–dependent Photodissociation of $[Fe(bpy)_3(CH_3OH)_n]^{2+}$ Clusters, n=2–6, Triggered by Excitation of the Metal–to–Ligand Charge–Transfer Transition," J. Phys. Chem. A 101:1081–1092.

Spence et al. (1998), "Metal–to–Ligand Charge Transfer in the Gas–Phase Cluster Limit," J. Phys. Chem. A 102:6101–6106.

Svoboda, M and tom Dieck, H. (1980), "Diazadien–Nickel–Alkyle," J. Organomet. Chem. 191:321–328.

Taylor, S.J. and Morken, J.P. (Apr. 1998), "Thermographic Selection of Effective Catalysts from an Encoded Polymer–Bound Library," Science 280:267–270.

Whitheouse et al. (1985), "Electrospray Interface for Liquid Chromatographs and Mass Spectrometers," Anal. Chem. 57:675–679.

Wilson, S.R. and Wu, Y. (1993), "A Study of Nickel–Catalyzed Coupling Reactions by Electrospray Ionization Mass Spectrometry," Organometalics 12:1478–1480.

* cited by examiner

MASS SPECTROMETRIC SCREENING OF CATALYSTS

CROSS-REFERENCE TO RELATED APPLICATIONS

This application takes priority under 35 U.S.C. 119(e) from U.S. Provisional applications Ser. Nos. 60/117,205, filed Jan. 25, 1999 and 60/136,416, filed May 28, 1999 and also takes priority under 35 U.S.C. 119 from Swiss application CH125/99, filed Jan. 22, 1999. Each of these applications is incorporated by reference in its entirety herein to the extent that it is not inconsistent with the disclosure hereof.

BACKGROUND OF THE INVENTION

Described here is a rapid screening method for identifying compounds having catalyst activity which employs mass spectrometric analysis. The method is exemplified for rapid screening of polymerization catalysts using tandem mass spectrometry and gas phase ion-molecule reactions and is specifically applied to screening of organometallic catalysts used in the production of polyolefins. The screening method of this invention has the advantages of high sensitivity (mg-scale quantities), very short assay times (one hour), simultaneous competitive screening of multiple catalysts directly according to propensity for high polymer formation (rather than a derivative property such as heat release), good prospects for scaling to large combinatorial libraries, and implicit encoding of catalyst identity by mass. Simple ion-molecule reactions are used to simplify the mass spectrum of complicated mixtures generated during screening.

The identification, preparation and testing of individual catalysts has been long pursued. The screening of catalyst libraries to identify new and improved catalysts is a recent phenomenon. Screening of libraries of compounds, which may have been combinatorially generated, has been extensively applied in biological systems and for the identification of potential therapeutic agents. Methods for high-throughput combinatorial screening of organometallic catalysts now occupy a central position in the emerging area of combinatorial materials science. (A general review of screening for catalysts has recently appeared: Jandeleit, B. et al. (1998) Cat. Tech. 2:101). A variety of strategies have been employed to implement catalyst screening by correlating some aspect of catalysis to a measurable quantity. Preferred screening strategies are those that are rapid and which can be applied to assess very small samples. Chromatographic (Francis, M. B. (1999) Angew. Chem. 111:987), thermographic (Taylor, S. J. and Morken, J. P. (1998) Science, 280:267; Reetz, M. T. et al. (1998) Angew Chem. 110:2792), fluorescence quenching (Cooper, A. C. et al. (1998) J. Am. Chem. Soc. 120:9971), microwell parallel reactions (Burgess, K. et al. (1996) Angew. Chem. 108:192; Senkan, S.M. (1998) Nature 394:350), and polymer-supported "Bead" methods (Cole, B. M. et al. (1996) Angew. Chem. 108:1776; Boussie, T. R. et al. (1998) Angew. Chem. 110:3472) have been applied with varying degrees of success. Only the polymer-supported bead methods have been applied to identify organometallic catalysts for polymerization reactions, the other methods being inapplicable for a variety of technical reasons. Even the polymer-supported bead method, when applied to polyolefin catalyst screening, suffers from a clumsy encoding procedure that limits its usefulness.

Catalyst screening strategies typically assay reaction rate or turnover number by rapid assay of the products of a catalyzed reaction. The emphasis is on the miniaturization and acceleration of methods used conventionally for product determination. For example, rate is correlated with heat release in the thermographic assay, which is appropriate for assays of overall catalytic activity. For polymerization reaction catalysts (Recent advances in new homogeneous Ziegler-Natta catalysts have been reviewed: Britovsek, G. J. P. et al. (1999) Angew. Chem. 111:448), on the other hand, overall catalytic activity is only one of several important catalyst properties for which high-throughput screens are needed. The key properties of polymerization products: average molecular weight ($M_w$, the weight-average molecular weight, or $M_n$, the number-average molecular weight) and molecular weight distribution ($M_w/M_n$, a measure of polydispersity because $M_w$ emphasizes the heavier chains, while $M_n$ emphasizes the lighter ones) are currently not accessible in any fast assay. The usual methods used to assess these properties of polymers, e.g., size-exclusion chromatography (also termed gel permeation chromatography or gpc), light scattering, viscosity, or colligative property measurement, require bulk samples and/or careful calibration, and are poorly suited to high-throughput screening.

SUMMARY OF THE INVENTION

The present invention provides methods for screening catalysts using mass spectrometric analysis of catalyst-bound intermediates in the catalytic cycle, or products of catalysis. The methods are applicable, in particular, to screening of organometallic compounds for catalytic function. Moreover, the methods are applicable, in particular, to screening for catalysts for polymerization reactions. More specifically, the methods employ a two stage (or two step) mass spectrometric detection method in which ions formed in a first stage ionization and which are linked to catalyst performance are selected and the catalyst associated with the selected ion is identified in a second stage employing tandem mass spectrometry. In specific embodiments, the screening methods of this invention avoid explicit encoding because the identity of the catalyst is implicitly contained in the product molecular mass (typically an intermediate product), since the catalyst (or a portion thereof) remains attached to the product.

The methods of this invention are particularly beneficial in screening for polymerization catalysts to avoid spectral congestion that can be created by the distribution of product oligomer and polymer lengths even for analysis of the polymerization products of a single catalyst species. Further, the screen, as applied to polymerization catalysts, is direct in that it assays polymer chain growth itself rather than a property which may be correlated with chain growth.

In the methods of this invention, one or more test catalysts are provided. The test catalysts are contacted with a selected reactant species under selected reaction conditions. The reagent species is a compound or mixture of compounds upon which the catalyst acts to generate a desired product. Reaction conditions are selected to promote a selected catalytic reaction. The catalytic reaction is quenched after a selected time sufficient to allow the selected reaction to proceed to generate product, e.g., for polymer chains to grow, and allow differentiation of catalyst activity. After quenching, the reaction mixture is introduced into the first stage of a tandem mass spectrometer, subjected to ionization, and mass analysis. Prior to introduction into the mass spectrometer, the quenched reaction mixture can optionally be subjected to partial purification, solvent removal, dilution, concentration, or chemical derivatization to improve analysis, remove impurities or the like.

Certain ions formed in the first stage of the tandem mass spectrometer are selected for introduction into the second stage of the spectrometer. Ions are selected which derive from the catalyst activity that is being screened. For example, in screens for polymerization catalysts ion mass selection can be employed, i.e. ions with mass/charge ratio (m/z) greater than a selected cutoff mass can be selected as derived from the best catalysts, e.g., those that promote the longest chains in the time given. The selected ions are introduced into the second stage of the mass spectrometer where they are subjected to a reaction to give daughter ions that allow identification of the catalyst which catalyzed formation of the products whose ions were selected from the first stage. For example, again in polymerization reactions, the selected high mass ions, associated with the longest polymer chains formed, are subjected in the second stage to reactive collisions with neutrals to generate daughter ions. Ion-molecule reactions, including collision-induced dissociation, can be employed to generate daughter ions. Preferred ion molecule reactions are those which cleave the product, e.g., the polymer chain, from its associated catalyst or portion of the catalyst, leaving an ion that can be directly, and preferably, uniquely related to the catalyst. Mass analysis of the daughter ions generated allows identification of the catalyst species responsible for the products from which the selected ions derive.

The test catalysts can be provided as a library encompassing a plurality of compounds spanning a range of structural variants to assess the relationship of structure to catalytic function. For example, a library of candidate polymerization catalysts is contacted with a selected monomer under reaction conditions (pH, temperature, solvent, etc.) that promote polymerization. In specific embodiments, the reaction mixture sample is introduced into the mass spectrometer in a manner that preserves association of the catalyst with the reaction product(s), e.g., the catalyst (or a portion thereof) remains associated with the growing polymer chain formed from reagent monomers in a polymerization reaction.

In specific embodiments, the mass spectrometric methods of this invention can also be employed to obtain bulk properties of polymers that result from the use of a catalyst. The average molecular weight and molecular weight distribution of all polymer chains, not just metal-bound (i.e., catalyst bound) polymers can be determined by the generation of kinetic data (as provided in Example 3). Distributions of odd chains (metal-bound oligomer chains with methyl endgroups) and even chains (metal bound oligomer chains with hydrogen endgroups) are observed in the mass spectrum after catalytic reaction. Fitting of the experimental odd/even distribution data with the general kinetic scheme for Ziegler-Natta polymerization yields absolute rates for initiation, propagation, and chain-transfer for a set of reaction conditions. These rates allow determination of average molecular weight and molecular weight distribution of products from catalytic reaction of screened catalysts without explicit preparation or isolation of bulk polymer. Average molecular weight and molecular weight distribution of polymeric products can be used as screening criteria for catalyst selection.

The method of this invention is particularly suited to screening of ionic and/or ion pair polymerization catalysts. A library of catalysts consisting of more than two distinct catalysts is contacted with an excess of monomer, usually ethylene, but which can be other simply substituted olefins, in organic solution. The reaction is then quenched with an additional ligand, such as CO, isocyanides, ethers, esters, phosphites, sulfoxides or other coordinating ligands, after polymerization has proceeded up to addition of a few hundred monomer units. The resulting quenched solution is then electrosprayed into a tandem mass spectrometer. The high mass ions which are associated with the catalyst (or a portion of the catalyst) linked to the longest polymer chains formed during the reaction are selected in the first stage of the mass spectrometer. These selected ions will be associated with the more active catalysts. The selected ions are then subjected in the second stage of the spectrometer to an ion-molecule reaction, e.g., collision-induced dissociation, to cleave off the oligomer/polymer chain from the catalyst. The daughter ion(s) remaining after the ion-molecule reaction is mass-analyzed in the second stage of the mass spectrometer identify the catalyst species responsible for the production of the highest molecular weight polymer chains. The drastic simplification of the mass spectrum by means of an ion-molecule reaction is a unique feature of this invention. Parent ion scans on a particular daughter mass allows the extraction of polymer distributions and the determination of kinetic parameters for one of the catalysts, in the presence of the others.

DETAILED DESCRIPTION OF THE INVENTION

Figure 1:
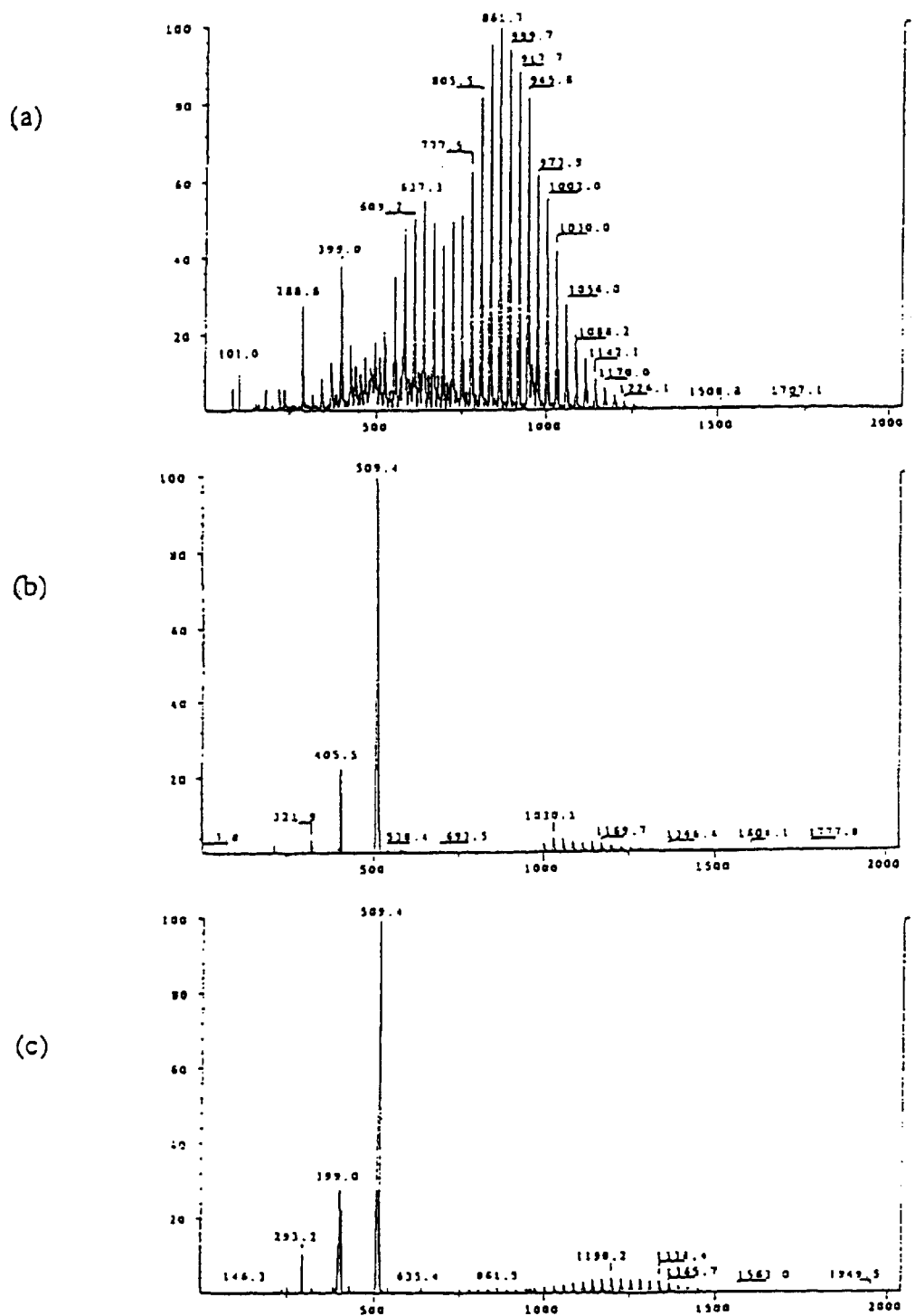
FIG. 1A is an electrospray mass spectrum of a quenched and diluted reaction mixture of complexes 1a–1c each approximately $10^{-3}$ M in $CH_2Cl_2$ saturated with ethylene. The reaction was allowed to react at –30° C. for 1 hour before quenching with DMSO and 100-fold dilution. The quenched and diluted reaction mixture was electrosprayed in a Finnigan MAT TSQ-7000 tandem mass spectrometer. The spectrum of this figure was recorded by scanning the first quadrupole. The mass spectrum contains several series of polymeric ions and is very complex.
FIGS. 1B and C are daughter ion mass spectra of the quenched reaction mixture of FIG. 1A with the first quadrupole set to reject ions below m/z 1000 and below m/z 600, respectively, and in which the remaining ions were subjected to collision-induced dissociation with xenon (~0.5 m Torr) at a nominal ion energy of 40 eV.

This invention provides methods based on mass spectral analysis for screening and selection of compounds for catalytic activity or improved catalytic activity. The methods can be used to identify compounds that are catalysts for a selected reaction from among a plurality of test catalysts or to identify improved catalysts from a plurality of known catalysts. The methods can be applied to a library of compounds having no known activity to catalyze a selected reaction or can be applied to a library of compounds known to have a given activity. In the latter case, the methods can identify, among known catalysts, those that have the greatest activity or those which generate products having a desired structure or property. The methods are particularly useful for screening compounds for activity as polymerization catalysts or for screening a set of likely catalysts to select those having the greatest activity, e.g., for those promoting the fastest or most efficient reactions.

In this invention, catalysts (or identifiable parts of catalysts) which remain associated with a growing polymer chain, at least part of the time, can be screened. The catalyst remains associated, i.e., bonded, in some way to the growing polymer chain. The association between the catalyst and the polymer chain may be through covalent, ionic or hydrogen bonding, so long as the association is not substantially disrupted during introduction of the sample into the mass spectrometer. The method of this invention is particularly well suited to screening of organometallic complexes as catalysts where the product of catalysis remains associated (at least for some time) with the organometallic catalyst.

In this invention, for application to polymerization catalysis, bulk polymer properties such as $M_w$ or polydispersity $M_w/M_n$ can be determined for the polymeric products of a given polymerization catalyst. These properties can be determined for reaction by one test catalyst or multiple test catalysts and used to select or identify a catalyst with desired activity.

Test catalysts in a library to be screened are typically structurally distinct, but more generally are distinct in that they exhibit unique mass spectra, i.e., exhibiting one or more unique ions which allow distinct catalysts to be ultimately identified in the second stage daughter ions. A library may also contain a portion of catalysts which although structurally distinct, are not necessarily distinct by mass spectrum. In this case, the screening method of this invention results in the identification of a set (preferably a small number) of test catalysts which includes at least one catalytically active species. The set members identified must then be further screened to determine which member or members of the set are, in fact, catalysts. The second screening can be performed in a variety of ways, for example, by simply assessing individual performance of the catalysts of the set in separate polymer reactions. The method will also allow the identification of the best catalyst or the better catalysts among the set of catalyst identified.

Distinct test catalysts of the library may be structurally similar, but possess different substituents (number, type) or different ligands (number, type). Test catalyst libraries may include distinct members that are homologs, isomers, enantiomers and like related structures. The screening method is particularly appropriate for screening of organometallic catalysts in which library members may differ in metal, valence state, ligands, or ligand substitution.

A library of catalysts can be prepared by well-known methods of synthesis, including combinatorial methods, employing readily available starting materials. Libraries can include known catalysts which are assayed for their relative activity or potential catalysts which are screened for the presence of activity or to select for the most active catalysts.

The term "reaction product" is generically used herein to refer to any product, whether an intermediate or final product, and whether or not the product is bound to a catalyst (or a portion of a catalyst). An intermediate product refers to any chemical species, whether or not it is bound to catalyst, which is a precursor to a final product. A final product is the ultimate product (which may represent a mixture of chemical species) which would result from complete reaction of test catalyst(s), reactant compounds(s) and any activator or coreactant present in the reaction mixture under the assay conditions (solvent, temperature) if the reaction were allowed to go to completion.

For screening assays herein the reaction mixtures are preferably quenched before completion of reaction. Further, in the assays herein, the reactant compound or compounds are typically in excess to avoid their depletion prior to quenching. In polymerization reactions, the final product is typically a bulk polymer and the intermediate products are oligomers and polymer chains that would grow into the bulk polymer if the reaction proceeded to completion.

The test reaction, e.g., the polymerization reaction, conditions can be varied (e.g., pH, temperature, or solvent) to identify preferred reaction conditions for a given catalyst or to select the best catalyst for given reaction conditions. The test reaction is allowed to proceed for a sufficient time before quenching to allow differences in catalyst activity to be detected. In polymerization catalyst screens, the reaction is preferably allowed to proceed in the presence of excess monomer until from about 25 to several hundred monomers are added to the growing polymer chain.

The test reaction sample, e.g., the polymerization reaction mixture, is preferably introduced into the first stage of the mass spectrometer using atmospheric pressure ionization and more preferably using electrospray ionization.

In specific examples electrospray ionization tandem mass spectrometry (ESI-MS/MS) and gas-phase ion-molecule reactions have been used for the rapid screening of Brookhart-type Pd(II) olefin polymerization catalysts (Johnson, L. K. et al. (1995) J. Am. Chem. Soc. 117:6414; Johnson L. K. et al. (1996) J. Am. Chem. Soc. 118:267). Much of the basic chemistry of the diimine complexes was explored by Svoboda, M. and tom Dieck, H. (1980) J. Organomet. Chem. 191:321; tom Dieck, H. et al. (1981) Z. Naturforsch 36B:823.

While electrospray ionization mass spectrometry (A complete monograph on the technique is: *Electrosplray ionization Mass Spectrometry*, R. D. Cole, Ed., John Wiley: New York, 1997) has been extensively applied to the biopolymers since the introduction of the technique by Fenn and coworkers (Whitehouse, C. M. et al. (1985) Anal. Chem. 57:675), applications to organometallic chemistry have come only recently. Straightforward analytical applications were first reported by Chait (Katta, V. et al. (1990) J. Am. Chem. Soc. 112:5348), Colton and their co-workers (Colton, R. and Traeger, J. C. (1992) Inorg. Chim. Acta 201:153; work from this group has been reviewed: R. Colton, et al. (1996) Mass Spec. Rev. 14:79). Mechanistic studies of ion-molecule reactions by electrosprayed organometallic ions have been addressed by the present group (Hinderling, C. et al. (1997) Angew. Chem. 109:272; Hinderling, C. et al. (1997) J. Am. Chem. Soc. 119:10793; Feichtinger, D. and Plattner, D. A. (1997) Angew. Chem. 109:1796; Feichtinger, D. et al. (1998) J. Am. Chem. Soc. 120:7175; Hinderling, C. et al. (1998) Angew. Chem. 110:2831) and by Posey and coworkers (Spence, T. G. et al. (1997) J. Phys. Chem. A 101:139; Spence, T. G. et al. (1997) J. Phys. Chem. A 101:1081; Spence, T. G. et al. (1998) J. Phys. Chem. A 102:6101). Further applications from a few other groups (Wilson, S. R. and Wu, Y. (1993) Organometallics 12:1478; Aliprantis, A. O. and Canary, J. W. (1994) J. Am. Chem. Soc. 116:6985; Kane-Maguire, L. A. P. et al. (1995) J. Organomet. Chem. 486:243; Lipshutz, B. H. et al. (1996) J. Am. Chem. Soc. 118:6796) have also appeared, with two groups (Dzhabieva, Z. M. et al. (1996) Russ. Chem. Bull. 45:474; Saf, R. et al. (1996) Macromol. 29:7651) investigating polymerization reactions. Neither group attempted, however, to examine more than one catalyst at a time. The mass spectra were furthermore so complicated by the distribution of oligomeric and/or polymeric ions originating from even a single catalyst as to preclude any possibility of screening. The present application is the first instance of ESI-MS/MS as an assay of multiple, competitive, simultaneous, catalyzed reactions in solution. A unique feature of the method of this invention is the use of an ion-molecule reaction, simple CID (collision-induced dissociation) in this instance, to simplify the otherwise dauntingly complicated mass spectrum of a mixture of polymers.

The combination of sensitivity, speed, direct assay, and versatility demonstrated in this pilot experiment means that one can screen large (n>>100) libraries of combinatorially-generated catalysts. The availability of autosamplers for electrospray mass spectrometers facilitates automation of the screening process.

In the general mechanism for homogeneous Ziegler-Natta polymerization, the limiting chain length, and therefore the polymer molecular weight, is determined primarily by the ratio of the propagation rate to the chain-transfer rates. Whereas the former rate can be measured by a number of techniques, there are extremely limited ways to obtain the latter. Brookhart reported propagation rates (Johnson, L. K. et al. (1995) J. Am. Chem. Soc. 117:6414) for catalysts related to 10. In control experiments on these catalysts, our propagation rates were approximately a factor of two slower than that in the literature. Given that the mode of activation was different, giving triflate as the counterion in the present work, as opposed to tetrakis(pentafluorophenyl)borate, the factor of two is completely understandable. Brookhart reports no chain-transfer rates, so no direct comparison can be made. One could proceed to compute the polymer molecular weight to compare to the $M_w$ reported in the literature, but that value was measured under conditions which are far from ideal for the comparison, e.g., 45 g polymer formed in 100 ml solvent, making a direct test again difficult. Nevertheless, one should note that 10 was not rated as one of the better catalysts in the Brookhart work, consistent with the modest $M_w$ seen in FIG. 6.

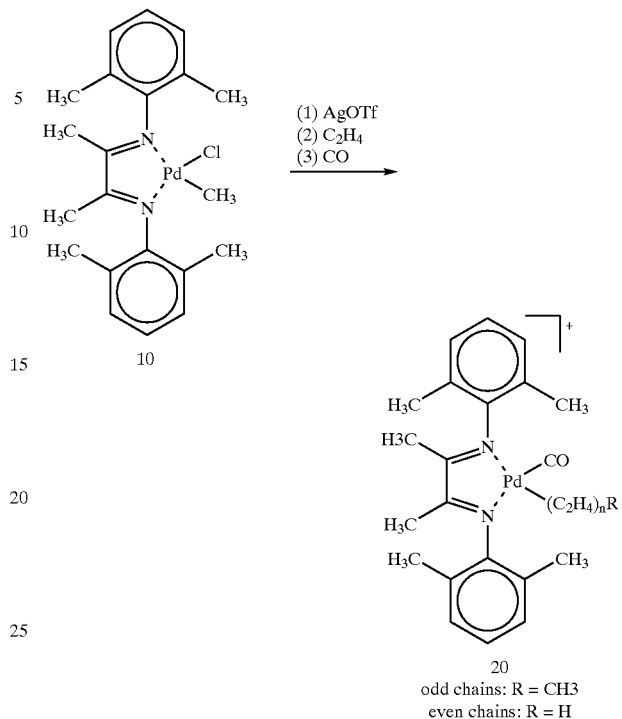

Figure 4:
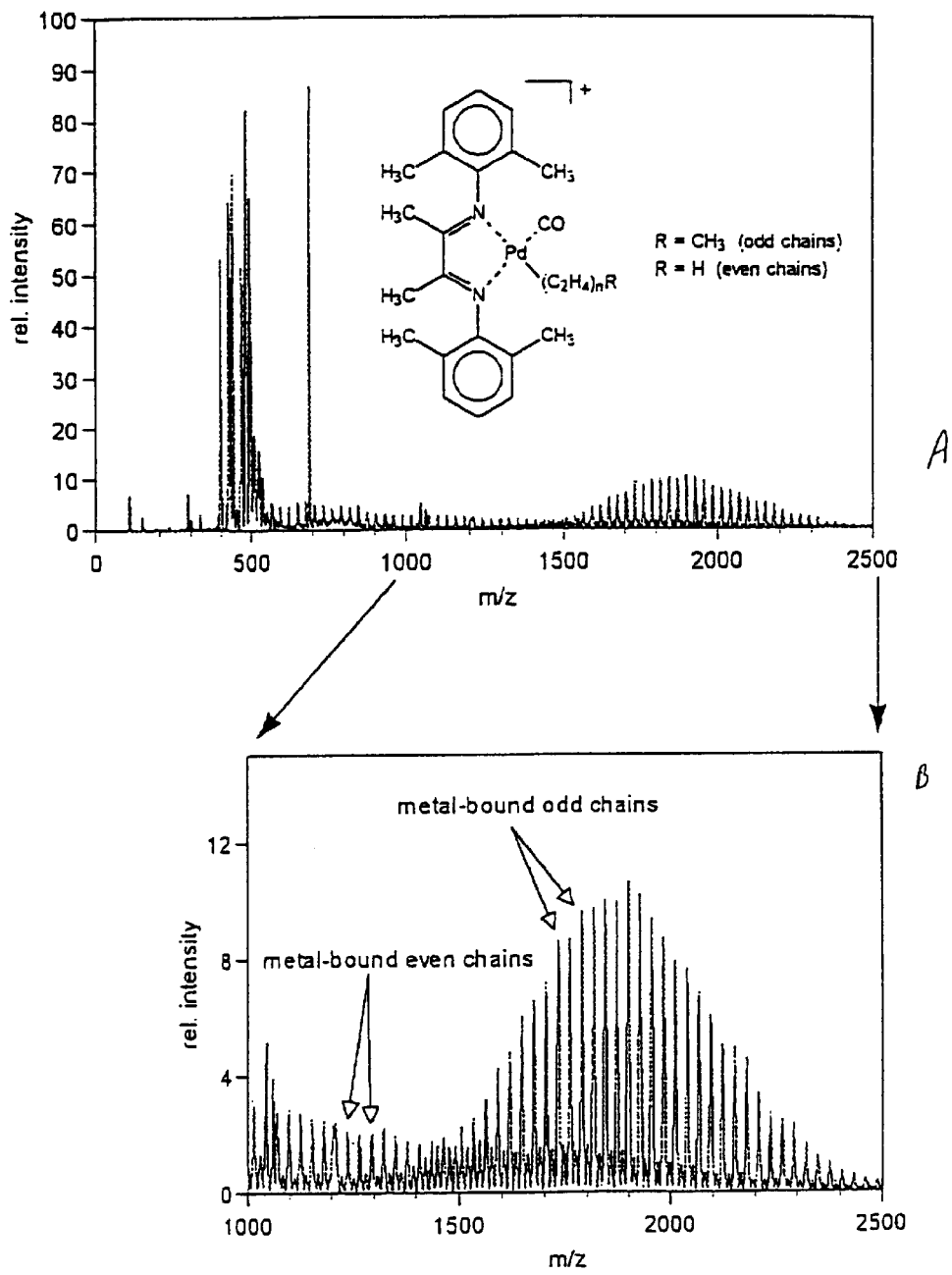
FIG. 4A is an electrospray mass spectrum of a quenched and diluted reaction mixture of procatalyst 10 ($4.45 \times 10^{-3}$ M in $CH_2Cl_2$), saturated with ethylene and activated with AgOTf as described in Example 3. The mass spectrum illustrates envelops of metal-bound odd and even chain ions.
FIG. 4B is an enlargement of the m/z 1000–m/z 2500 region of the mass spectrum of FIG. 4A.

Procatalyst 10 was chosen for the test because it gave odd-chain and even-chain distributions which are easily seen in FIGS. 4A and 4B. If a better catalyst were to be used (The catalyst with o,o'-diisopropyl rather the o,o'-dimethyl groups on the aromatic moieties gives exceedingly small peaks corresponding to even-chain distribution, consistent with it being the best of the reported catalysts), the same exercise could be done to extract the three rates, but the difference in magnitude between the odd-chain and even-chain distribution would have been greater. With commercial quadrupole or sector instruments delivering a dynamic range of ~10,000-to-1, one can estimate that the present screening method should function up to $M_w$~500,000. the upper-bound applies only if one is in fact concerned with using the mass spectrometric method to quantify $M_w$. In practice, as a screening method, only trends and gross magnitudes need to be measured, because the actual polymer molecular weight would be determined conventionally for a "hit" anyway. This same argument applies in case the actual rates for propagation and chain-transfer, contrary to assumption, do in fact depend on chain length. As long as the variation is smooth and slow as a function of chain length, the integrity of the mass spectrometric screen is not impaired.

Ideally, one would want the three rates in the fit to the odd- and even-chain distributions to be linearly independent so that a unique fit can be achieved. While an analytical proof of linear independence has not been done, an examination of the behavior of the fitting functions as the parameters are varied suggests that the three rates can be uniquely determined. Qualitatively, the absolute propagation rate is primarily responsible for the position of the maximum and the shape of the leading edge of the odd distribution. The ratio of propagation to initiation rate determines the width and the shape of the trailing edge of the odd-chain distribution. The ratio of the propagation to chain-transfer rate determines the relative magnitudes of the odd- versus even-chain distributions. The shapes—bell-shaped for the odd-chain distribution, and monotonically decreasing with a sharper drop at the leading edge for the even-chain distribution—are consequences of the kinetic model and not otherwise adjustable. The good fit of these shapes with the three rates suggests that the model is adequate for the deconvolution.

Important for the interfacing of the assay to a complete screening procedure is the ability of the assay to handle a pooled screen, i.e., multiple simultaneous catalysts at once, and the facility by which the assay can be automated for a parallel screen. For both kinds of screens, the mass spectrometric method is well-suited. For a parallel screen, automation can be done with autosamplers available for the commercial spectrometers. Compared to conventional methods for polymer molecular weight determination, the present mass spectrometric method is faster, requires much less sample, and is more amenable to automation. Other mass spectrometric approaches (mass spectrometric approaches to polymer characterization have been described: Lorenz, S. A. et al. (1999) Appl. Spec. 53:18A; Festage, R. et al. (1998) J. Am. Soc. Mass Spec. 9:;299; Hunt, S. M. et al. (1998) Anal. Chem. 70:1812; Jackson, C. A. and Simonsick, W. J. (1997) Curr. Opin, Solid State Mat. Sci. 2:661) suffer from the disadvantage that they operate directly on the polymer rather than on the metal-bound oligomers, meaning that the ionization process (in the case of electrospray) and/or the mass range of the spectrometer (for electrospray or MALDI), become problematic, especially for polyethylene and polypropylene. This is a specific instance of the advantage offered by the method of this invention where the assay is based on the catalyst-bound intermediates as opposed to assay of final bulk products.

As in many of the Ziegler-Natta catalysts, the final polymer molecular weight is largely determined by chain-transfer with monomer (or polymer, if the concentration becomes high enough). The elementary steps in the polymerization (a complete overview of Ziegler-Natta polymerization can be found: *Ziegler Catalysts*, Fink, G. et al. (ed.), Springer-Verlag, Berlin, 1995) have been explored computationally by Ziegler and co-workers (Margl., P. et al. (1999) J. Am./Chem. Soc. 121:154 and references therein), and experimentally for this particular family of catalysts by Brookhart. Because of very fast monomer complexation, the resting state of the Pd(II) diimine catalysts is the ethylene complex; the ethylene consumption rate was found accordingly to be zero-order in ethylene (Johnson, L. K. et al. (1995) J. Am. Chem. Soc. 117:6414).

Figure 5:
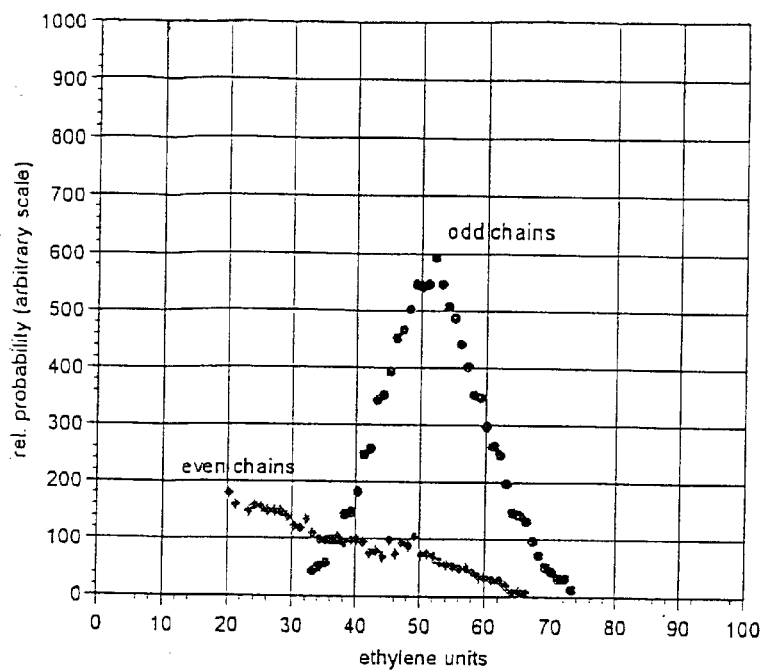
FIG. 5 is a graph of the fit of odd and even chain distributions obtained from the mass spectra of FIGS. 4A and B to determine the rates of initiation, propagation and chain transfer for the catalytic reaction. See Example 3.

A thermostated $CH_2Cl_2$ solution (5 ml, 9.8° C.), presaturated with ethylene, in which 2 mg (<5 $\mu$mol) of 10 was dissolved, was activated by AgOTf, allowed to polymerize for 26 minutes, and then quenched by saturation with CO gas (several neutral two-electron ligands, such as DMSO and pyridine, were tried as quenchers. CO gave the most reliable results). A sample was removed, diluted to fifty-fold, and analyzed by electrospray in a modified Finnigan MAT TSQ-7000 mass spectrometer. The instruments and operating parameters have been previously described (Hinderling, C. and Chen, P. Angew. Chem., in press; Hinderling, C. et al. (1997) Angew. Chem. 109:272; Hinderling, C. et al. (1997) J. Am. Chem. Soc. 119:10793; Feichtinger, D. and Plattner, D. A. (1997) Angew. Chem. 109:1796; Feichtinger, D. et al. (1998) J. Am. Chem. Soc. 120:7175; Hinderling, C. et al. (1998) Angew. Chem. 110:2831; Kim, Y. M. and Chen, P. (1999) Int. J. Mass Spec. 185–7:87). The resulting mass spectrum is shown in FIG. 4A. Examination of the m/z= 1000–2500 region (FIG. 4B) reveals two distinct distributions of oligomeric ions. Metal-bound oligomer chains with methyl end groups, designated odd chains, correspond to chains built on a catalytic center that has not undergone chain-transfer. Metal-bound oligomer chains with hydrogen endgroups, designated even chains, correspond to chains built on a catalytic center that has undergone chain-transfer at least once. Although both the odd and even chains are built by addition of ethylene units, they are displaced from one another by 14 mass units. Using the general kinetic scheme for Ziegler-Natta polymerization, with adaptations to the specific class, in this case Brookhart catalysts, the two distributions can be fitted, by integration of the differential rate equations, to yield unique, absolute rates for initiation, propagation, and chain-transfer for the particular set of conditions in the reaction. The fit for $k_{init}$=0.01, $k_{prop}$=0.044, and $k_{trans}$=0.00045 sec$^{-1}$, for initiation, propagation, and chain-transfer rates, respectively, is shown in FIG. 5. The entire procedure can be repeated at several temperatures to obtain rates for Arrhenius plots. A preliminary attempt in this direction finds non-Arrhenius behavior for the initiation rate, understandable because it is heterogeneous; we find, on the other hand, $E_a^{prop}$=18.9 and $E_a^{trans}$=21.4 kcal/mol. The rates can also be used to compute the average molecular weight and extent of polymerization as a function of time, shown in FIG. 6, under the assumption of constant ethylene concentration and dilute polymer solution. With these assumptions, the polydispersity is $M_w/M_n$=2, as expected from theory. In the event that more realistic conditions, e.g., high polymer concentration, need to be simulated, the rate expressions with chain-transfer to either monomer or polymer can be integrated. One expects in such a case that $M_w/M_n$>2.

The methods herein have been described employing conventional tandem mass spectrometry, but can be implemented employing other mass spectrometric methods known in the art which allow separation of initially generated ions by mass and further analysis of the selected ions. Ions can be generated by a variety of ionization methods known in the art. The methods of ionization appropriate for use in this screening method provide ions in which the catalyst (or a portion of the catalyst) remains associated with the reaction product on initial ionization. Further, the ionization method chosen preferably does not invalidate the selection criteria, e.g., in polymerization catalyst screening, the initial ionization method employed does not itself substantially affect ion polymer chain length.

Catalyst screening methods specifically exemplified herein rely on selection of higher mass-to-charge ratio ions associated with the longest polymer chains formed in the mass/charge test reaction. Other ion selection criteria may be applied to the ions formed in the first stage of the mass spectrometer. For example, an intermediate range of ion masses may be selected, or a particular ion or set of ions associated with a desired type of chain branching may be selected as can happen when electrospray or MALDI is used for the direct mass spectrometric analysis of high polymers.

Screening for polymerization catalysts is preferably based on an assay or prediction of the properties of the bulk polymer produced by a given catalyst under given conditions. The high-throughput screening procedures available to date assay only according to rate of reaction, i.e. catalyst activity, which is one of the less important properties. Average molecular weight and its distribution, in the bulk polymer, are the generally more important criteria for screening for polymerization catalysts.

This invention also provides a method by which electrospray ionization mass spectrometry is used to determine kinetic parameters from metal-bound oligomer distributions that predict the bulk polymer properties of material produced by the catalyst. Unique in this method is the observation and use of the so-called even- versus odd-chain distributions to determine the important ratio of propagation to chain transfer rates. This ratio is the single most important determinant of polymer molecular weight.

This methodology is applicable to other polymerization catalysts, for example (Palladium-based catalysts for olefin-CO copolymerization: Brookhart, M. et al. (1992) J. Am. Chem. Soc. 114:5894; Drent, E. and Budzelaar, P. H. M. (1996) Chem. Rev. 96:663; Iron and cobalt-based polyolefin catalysts: Small, B. L. et al. (1998) J. Am. Chem. Soc. 120:4049; Molybdenum and tungsten-based ROMP catalysts: Goodall, B. L. et al. (1993) J. Appl. Polymer Sci 47:607; McCann, M. et al. (1995) J. Mol. Catalysis A 96:31; Rhodes, L. F. European Patent 0 435 146A2 (1990); Mazany, A. M., European Patent 0 755 938 A1 (1995)).

Furthermore, the methods herein have application to catalyst selection in non-polymerization applications. In preferred applications of the method the catalyst (or a distinguishable portion of the catalyst) remains associated with a desired selected product on initial ionization.

This invention specifically relates to a method in which tandem mass spectrometry is used to assay or screen two or more catalysts for polymerization activity. The two stage mass spectrometric method described herein can also be used to assay or investigate the catalytic activity of individual catalysts. The invention also relates to the use of ion-molecule reactions, such as dissociative collisions, to simplify the mass spectrum of oligomer/polymer mixtures in a mass spectrometer. The mass spectrometric methods described herein can be generally employed to investigate polymerization reactions, for example the methods can be applied to determine the ratio of chain propagation to chain transfer in a given solution-phase polymerization reaction.

The general kinetic scheme for Ziegler-Natta polymerization is implemented by reference to the Mayl et al. (1999) reference and by application of standard computational methods know in the art. The numerical integration was performed by the POWERSIM (Modell Data AS) software package using standard methods, i.e., Euler's method or Runge-Kutta up to fourth-order. In each case, integration intervals were chosen so that the numerical method itself had a negligible effect on the outcome.

EXAMPLES

Example 1
Screening a Small Library of Brookhart Pd(II) Complexes with Different Aryl Groups on the Diilmine Ligand.

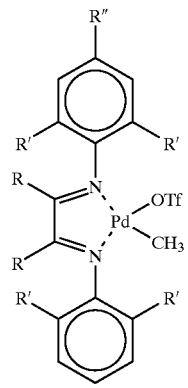

1a R = CH$_3$; R' = H; R" = H
1b R = CH$_3$; R' = CH$_3$; R" = H
1c R = CH$_3$; R' = CH(CH$_3$)$_2$; R" = H

The screening was performed according to the reactions in Scheme 1. A solution comprised of complexes 1a, 1b, and 1c (see Scheme 1), each at approximately $10^{-3}$ M in CH$_2$Cl$_2$, was saturated with ethylene and allowed to react at −30° C. for one hour, then quenched with dimethylsulfoxide (DMSO), and finally diluted one-hundred-fold. The solution was then immediately electrosprayed in a Finnigan MAT TSQ-7000 tandem mass spectrometer, operated as previously described (Hinderling, C. et al. (1997) Angew. Chem 109:272; Hinderling, C. et al. (1997) J. Am. Chem. Soc. 119:10793; Feichtinger, D. and Plattner, D. A. (1997) Angew. Chem. 109:1796; Feichtinger, D. et al. (1998) J. Am. Chem. Soc. 120:7175; Hinderling, C. et al. (1998) Angew. Chem. 110:2831). The electrospray mass spectrum, FIG. 1A, recorded by scanning the first quadrupole, was complex, showing a series of oligomeric and polymeric ions corresponding to each catalyst species with zero to approximately 50 ethylene units added. The first quadrupole, was then set to reject all ions with masses below a cutoff, either m/z=600 or m/z=1000. The remaining ions were collided against xenon (~0.5 m Torr) in an octopole ion guide at a nominal ion energy of 40 eV. The daughter ion spectra for the two different cutoffs, recorded by scanning the second quadrupole, are shown in FIGS. 1B and C, respectively. Clearly seen in FIG. 1B is the predominance of the mass peak corresponding to ion 3c and/or its daughter ion(s), formed by collision-induced elimination of the hydrocarbon chain from the ion built from catalyst 1c, indicating that 1c is the best polymerization catalyst of the three. When the mass cutoff is reduced from m/z=1000 to m/z=600, i.e., FIG. 1C, ion 3b and/or its daughter ion(s) appears, indicating that 1b is the second-best catalyst of the three. For the same three catalysts, 1a, 1b, and 1c, the ordering 1c>1b>1a has been previously reported (Johnson, L. K and Killian, C. M. (1995) J. Am. Chem. Soc. 117:6414). The agreement of the mass spectrometric and conventional assays demonstrates the efficacy of the new method for catalyst screening.

Example 2
Screening a Combinatorial Library of Brookhardt Pd (II) Complexes.

The eight complexes 1a–h (Scheme 1, where R. R' and R" are defined) in a test library were synthesized simultaneously by a modification of the literature procedure starting with an equimolar mixture of the eight individually-prepared diimine ligands (Kllegman, J. M. and Barnes, R. K. (1970) J. Org. Chem. 35:3140) in diethyl ether, reaction with one equivalent of [(cod)Pd(CH$_3$)(Cl)] (Rülke, R. E. et al. (1993) Inorg. Chem. 32:5769) at room temperature overnight, filtration of the orange precipitate, and activation of the solid products in CH$_2$Cl$_2$ solution with AgOTf.

Figure 2:
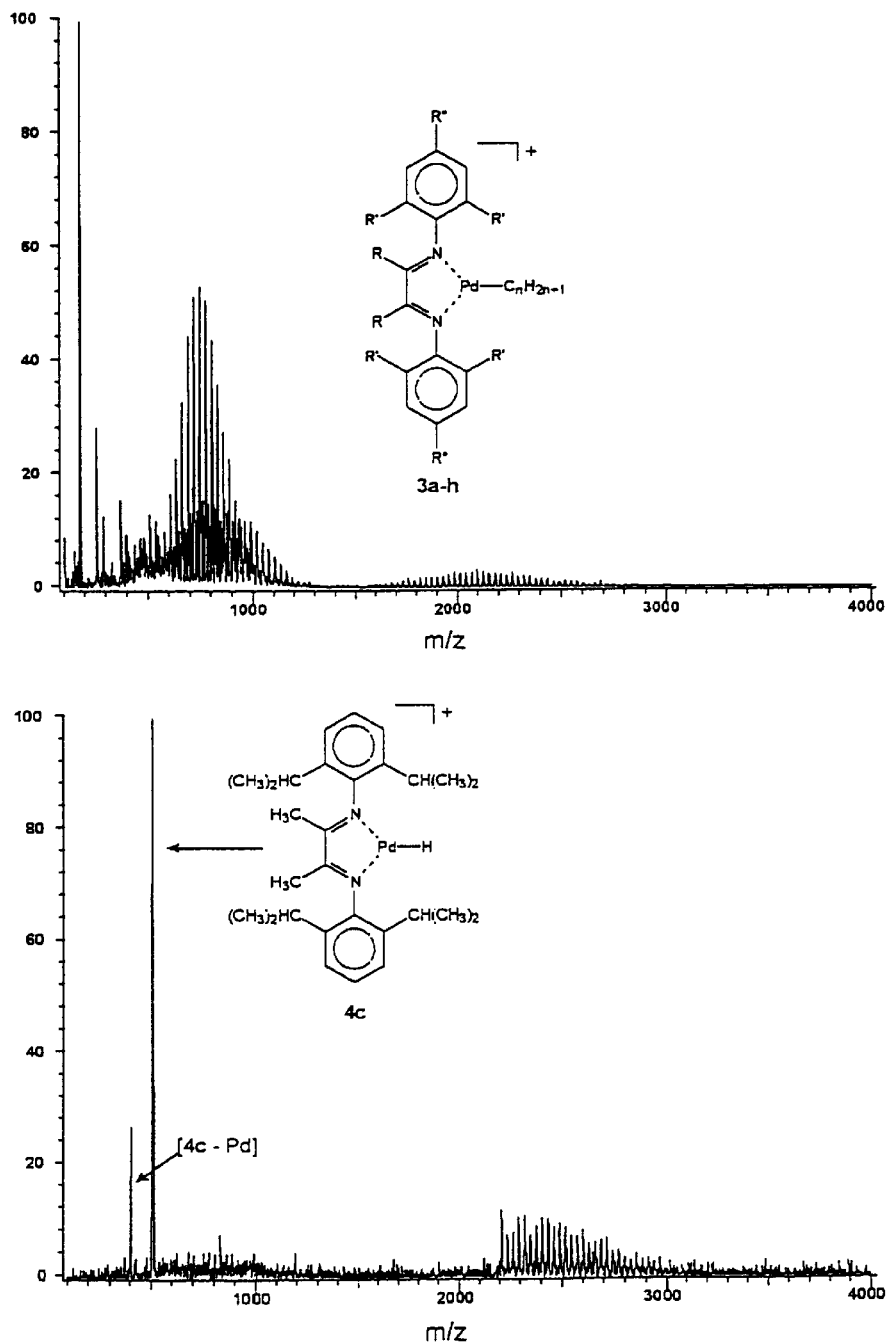
FIG. 2A is an electrospray mass spectrum of a quenched and diluted reaction mixture of complexes 1a–1h each approximately $10^{-3}$ M in $CH_2Cl_2$ saturated with ethylene. The reaction mixture was allowed to react at –10° C. for 1 hour before quenching and dilution. The quenched and diluted reaction mixture was electrosprayed in a Finnigan MAT TSQ-7000 tandem mass spectrometer. The spectrum of this figure was recorded by scanning the first quadrupole. The mass spectrum contains several series of polymeric ions and is very complex.
FIG. 2B is an electrospray mass spectrum of a quenched and diluted reaction mixture of 1c ($10^{-3}$ M in $CH_2Cl_2$ saturated with ethylene) illustrating the series of oligomeric and polymeric ions generated by a single catalyst.

Check of the catalyst mixture prior to activation by $^1$H NMR showed comparable concentrations of each of the eight complexes. The methyl resonances were sharp singlets, well-separated from each other and from other resonances. An electrospray mass spectrum (FIG. 2A) of the mixture of complexes (activated with AgOTf and then quenched with acetonitrile), showed 1a–h all to be present, again with comparable peak intensities. The solution comprised of the mixture, on the order of $10^{-3}$ M for each catalyst in CH$_2$Cl$_2$, was saturated with ethylene and allowed to react at −10° C. for one hour, then quenched by adding to a hundred-fold greater volume of 3% DMSO in CH$_2$Cl$_2$. The solution was then electrosprayed in a Finnigan MAT TSQ-7000 tandem mass spectrometer, as previously described in Example 1. The electrospray mass spectrum, recorded by scanning the first quadrupole, was complex, showing multiple, overlapping series of oligomeric and polymeric ions corresponding to each catalyst species with between zero and approximately one hundred ethylene units added, as seen in FIG. 2A. Additional complexity or broadening in the mass spectrum comes from the isotopic distribution in palladium (natural abundances are as follows: $^{102}$Pd 1.02%, $^{104}$Pd 11.14%, $^{105}$Pd 22.33%, $^{106}$Pd 27.33%, $^{108}$PD 26.46%, $^{110}$PD 11.72%) as well as the $^{13}$C satellite peaks (which become more prominent as the polymer grows), which is not resolved in the present mass spectra. When 1c alone is treated with ethylene, quenched, and analyzed by ESI-MS, the envelope of the oligomeric ions matches the predicted distribution based on the rate constants reported in Johnson, L. K. et al. (1995) J. Am. Chem. Soc. 117:6414; Johnson L. K. et al. (1996) J. Am. Chem. Soc. 118:267, as seen in FIG. 2B.

The first quadrupole was then set to radio-frequency-only mode, meaning that only ions above a given cutoff m/z ratio, in this case either m/z=2200 or m/z=1000, would be transmitted. It should be emphasized that high resolution is not needed at this step. The transmitted high-mass ions were collided against xenon (~0.5 mTorr) in an octopole ion guide at nominal ion energies between 30 and 80 eV. Representative daughter ion spectra for the two different cutoffs, recorded by scanning the second quadrupole, are shown in FIG. 3A and B, respectively.

Figure 3:
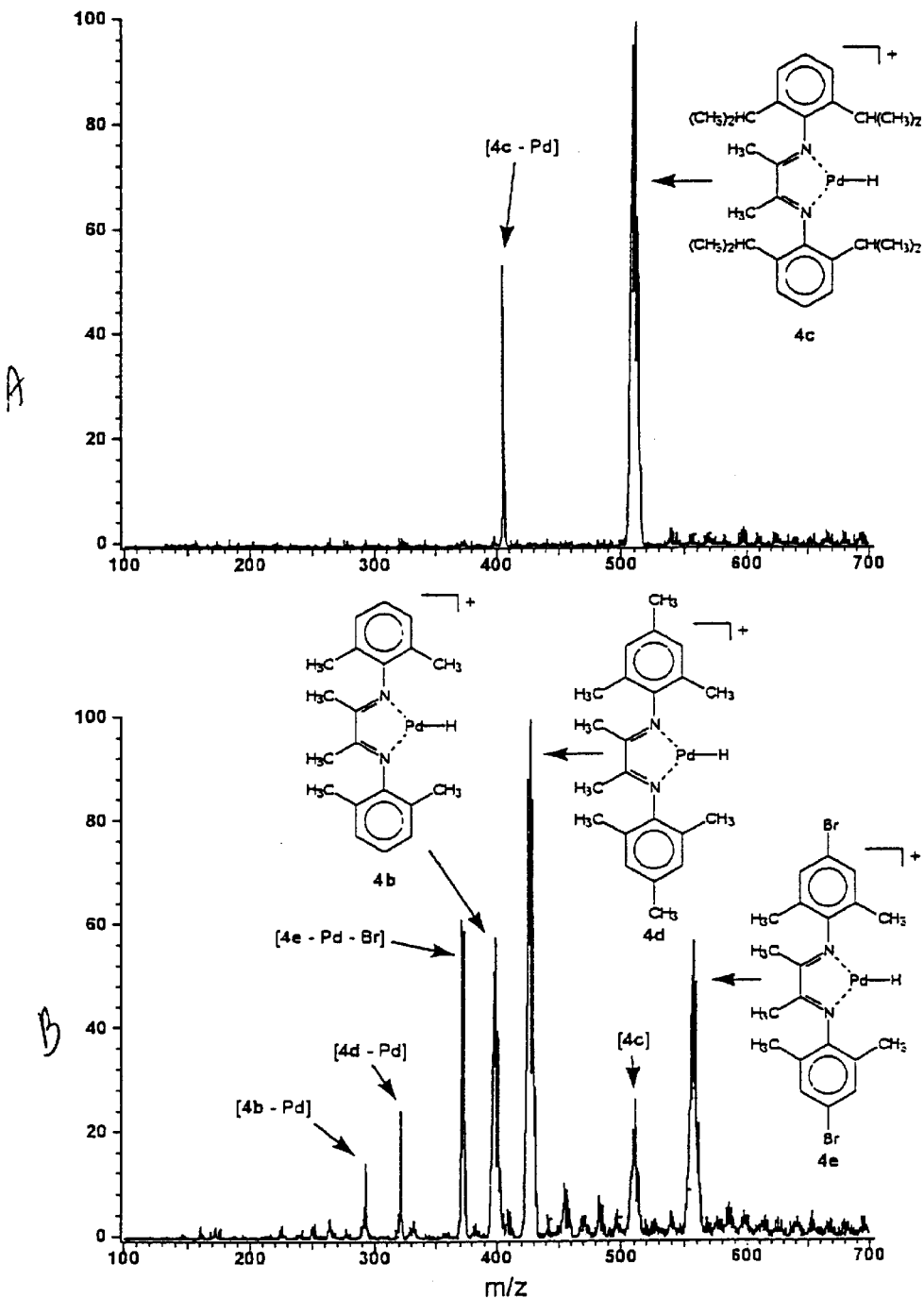
FIGS. 3A and B are daughter ion mass spectra of the quenched reaction mixture of FIG. 2A with the first quadrupole set to reject ions below m/z 2200 and below m/z 1000, respectively, and in which the remaining ions were subjected to collision-induced dissociation with xenon (~0.5 m Torr) at a nominal ion energy of 40 eV.

Clearly indicated in FIG. 3A is the predominance of the mass peak(s) at m/z=511, corresponding to ion 4c, formed by collision-induced β-hydride elimination of the hydrocarbon chain from the ion built from catalyst 1c. The small "sharp" peak at m/z=405 is a secondary fragmentation product corresponding to the diimine ligand without palladium. The secondary fragments [4-Pd] (or [4e-Pd-Br]) were unambiguously associated with the original ions 4 by performing parent ion scans on both 4 and the secondary fragment masses. The result clearly indicates, that of the eight potential catalysts, 1a–h, complex 1c is the best actual polymerization catalyst, in agreement with previous reports[1]. Similarly, the daughter ion spectrum with a lower mass cutoff shows (FIG. 3B) that the next best catalysts are 1b, 1d, and 1e. The agreement of the mass spectrometric and conventional assays demonstrates the efficacy of the method of this invention for catalyst screening. The ordering (1c>>1b~1d~1e>others) matches expectations based on the argument that P-hydride elimination (and hence chain transfer) is disfavored when steric considerations force the arene moieties to twist out-of-plane. The similarity between 1b, 1d, and 1e also suggests that electronic effects on catalyst efficacy are relatively small. Interestingly, 1g did not produce high polymers in the simultaneous screen, which was confirmed by assaying 1g individually. This result indicates that the isopropyl groups on the arene have little effect when the backbone of the 1,2-diimine ligand is unsubstituted. Brookhart did report reductions[1] in mean molecular weight (50×) and yield (5×) of polymer formed from 1g in comparison with that from 1c.

Example 3
Screening for Bulk Polymer Properties

In the previous examples, the mass spectrometric measurement analyzes oligomeric polyethylene chains that are attached to the cationic catalyst. On the other hand, once polymerization has proceeded to the bulk stage, most of the polymer chains are not metal-bound—they are products of chain-transfer and elimination, as evidenced by olefinic endgroups. The average molecular weight and molecular weight distribution of all polymer chains, not just for metal-bound ones, are desired criteria for catalyst selection. The ESI-MS/MS method provides this information by generating the kinetic data from which $M_w$ and $M_w/M_n$ for all polymer, metal-bound and metal-free, can be computed.

A solution of procatalyst (a precursor from which the active catalyst is generated) is saturated with ethylene and kept under a constant pressure of ethylene with efficient agitation to ensure that monomer concentration is unchanging. Activation in situ is done by addition of the appropriate activator. After a selected time, a quencher such as CO is added to halt polymerization. The solution is diluted to ESI concentrations and analyzed by ESI-MS/MS. The parameters of this screen are given in Scheme 3. Metal-bound oligomer chains with methyl endgroups, designated odd chains, correspond to chains built on a catalytic center that has not undergone chain transfer. Metal-bound oligomer chains with hydrogen endgroups, designated even chains, correspond to chains built on a catalytic center that has undergone chain transfer at least once. The odd and even chains form two distinct distributions displaced from one another by 14 mass units, with very different envelopes, visible in the mass spectrum (see FIG. 4A and the enlargement of the m/z 1000–2500 region in FIG. 4B). Using the general kinetic scheme for Ziegler-Natta polymerization by T. Ziegler (Scheme 4), with specific adaptations to the specific class, in this case Brookhart catalysts, the two distributions can be fitted to yield unique, absolute rates for initiation, propagation, and chain-transfer for the particular set of conditions in the reaction. By measuring the parameters for a given catalyst and activator at variable temperatures-importantly under dilute conditions-the rates obtained can be used to determine Arrhenius parameters for the three processes. These parameters then allow prediction of the bulk polymer properties of metal-free polymer formed by the catalyst under realistic conditions which could include reactivation of "dead" polymer (chain-transfer to polymer instead of monomer), chain-branching by 2,1 reinsertion, etc. We currently solve the coupled differential rate equations numerically, but are working on an analytical solution which will make the process much faster. Standard computation methods well-known in the art are employed.

Figure 6:
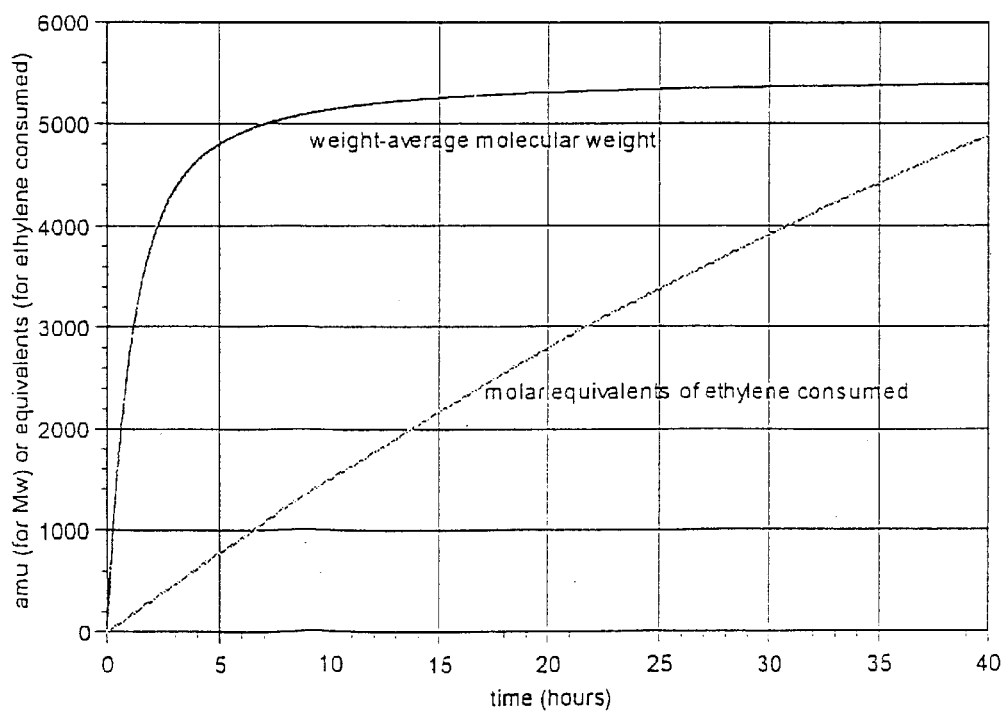
FIG. 6 is a graph of computed average molecular weight and extent of polymerization (indicated as molar equivalents of ethylene consumed) at 9.8° C. calculated using the rates of initiation, propagation and chain transfer determined from the fit to the odd- and even-chain distributions of the mass spectra of FIGS. 4A and 4B.

A not-very-good catalyst (Scheme 3) was intentionally chosen in this example so that the two distributions, i.e., odd and even, would be simultaneously visible in the raw data. FIGS. 5 and 6 show the quality of the fit. Similar measurements for a total of three temperatures give, for example, Arrhenius activation energies for propagation and chain-transfer of ~18.9 and 21.4 kcal/mol, respectively. For the propagation reaction, our value is about 1 kcal/mol lower than that reported by Brookhart for a slightly different catalyst (o,o'-diisopropyl instead of o,o'-dimethyl) with a different counterion and different solvent. Brookhart reports no chain-transfer rate data at all, but the $M_w$ extracted from our kinetic parameters compares well qualitatively to what one would expect from Brookhart's work.

As mentioned above, there is little data for a comparison. Moreover, the typical laboratory conditions under which bulk polymerization is done permits chain-transfer to polymer as well as to monomer because the polymer concentration can become quite high. As a result, both $M_w$ and especially $M_w/M_n$ become dependent on the details of how the polymerization was done. This can be built into the computation without much trouble, but it should be emphasized, that for the purpose of screening, the trends and the magnitudes of $M_w$ and $M_wM_n$ will be predicted well even without building these effects into the model.

Varying the three rates in the fit (FIG. 5) shows that the three parameters are close to linearly independent. The maximum of the odd chain distribution and its high-mass edge is largely determined by the absolute propagation rate. The width of the odd chain distribution is determined by the ratio of initiation to propagation rate. The relative magnitude of the odd chain vs. even chain distribution comes from the ratio of the propagation to chain-transfer rate. The shapes of the distributions comes from the kinetic model; the close resemblance of the fit curves to the experimental distributions indicates that the kinetic model has included all major effects.

For a catalyst which makes polymer of high $M_w$, the ratio of the odd chain to even chain distribution is also large. The upper-limit of $M_w$ for which the method should work is determined by the dynamic range of the mass spectrometric determination, i.e. how small a peak can be seen in the presence of a much larger neighboring peak. For transmission-type mass spectrometers, such as linear quadrupoles and sector instruments, commercial spectrometers have a dynamic range of ~10,000, meaning that $M_w$ up to 500,000 can be treated by this method. A further improvement could be achieved by use of a scintillation-based detector and 16- or 20-bit A-to-D converters. FT-ICR spectrometers are less suitable because the dynamic range on the FT-ICR is limited; both FT-ICR and quadrupole ion trap mass spectrometers will have problems because of poor statistics (less than 10,000 ions trapped at a time).

The mechanism from T. Ziegler relates the chain branching rate to the chain transfer rate, both reactions proceeding through the same transition state. We need to do the derivation in order to formulate the algorithm.

The polydispersity of the polymer in this example is $M_w/M_n=2$, which corresponds to a polymerization with chain-transfer limiting the chain length. The polydispersities in excess of two that Brookhart reports come from chain-transfer to polymer rather than monomer. In a typical experiment where $M_w/M_n\sim4$ was reported, he prepared 40 g polyethylene in 100 ml solvent. There is no question that, in the course of the polymerization, polymer became concentrated enough to compete with ethylene for the binding site on the catalyst. This effect is easily built into the integration code for the calculation, which means that concentration effects on the polydispersity can be predicted from the same dilute solution measurements that give $M_w$.

In our tests, MAO introduces a large number of low mass peaks and some underlying continuum of signals—the metal-bound oligomeric ions are nevertheless still visible. The interference could have made the clean acquisition of quantitative odd chain and even chain distributions difficult. However, the MS/MS method used previously—selection of oligomeric ions and then CID to produce the palladium hydride—easily circumvents the problem posed by MAO. If all ions are selected, and then subjected to CID, a parent scan done on the mass of the palladium hydride will give the odd and even chain distributions without any interfering MAO-derived peaks.

The chemical reaction part of the assay is, in principle, as fast or as slow as it would be for any assay using the same reaction. It should be noted that, since we are determining high polymer properties from measurements on metal-bound oligomers, we should be able to reduce the time for the chemical part of the assay in comparison to any assay which works with bulk polymer. The mass spectrometric part of the assay takes between 1 and 5 minutes.

The instruments employed in these assays can employ an autosampler. The autosampler can be operated anaerobically.

$CH_2Cl_2$ was distilled from $CaH_2$ before use. Electrospray-ionization was conducted with flow rates of 5 to 15 $\mu$l/min, $N_2$ sheath-gas, and a spray-voltage of 5.0 kV. Very mild desolvation-conditions (heated capillary 150° C., tube-lens potential 52 V) were employed. The procatalyst 10 was prepared by an art-known method as follows. The free diimine ligand, biacetyl-bis-(2,6-dimethylphenylimine) (Dieck, H. T. et al. (1981) Z. Naturforsch. 32b:823), 73.1 mg (0.25 mmol), and 66.3 mg (0.25 mmol) (1,5-cyclooctadiene)Pd(Me)(Cl) (Rülke, R. E. et al. (1993) Inorg. Chem. 32:5769) were suspended in 3 ml ether and stirred for 18 hours. The orange precipitate that formed was filtered off and washing thoroughly with ether and dried in vacuo. Yield 101.0 mg orange solid (90%).

$^1$H-NMR (300 MHz, $CDCl_3$) δ 7.17–7.05 (m, 6 H, Ar), 2.25 (s, 6 H, Ar—$CH_3$), 2.22 (s, 6 H, Ar—$CH_3$), 2.03 (s, 3 H, N=C—$CH_3$), 1.98 (s, 3 H, N=C—$CH_3$), 0.44 (s, 3 H, Pd—$CH_3$).

Polymerization experiments:

2.0 mg (4.45×10$^{-3}$ mmol) 10 were dissolved in 5 ml $CH_2Cl_2$ in a 20 ml Schlenk-tube fitted with a thermocouple to measure internal temperature and cooled to the reaction-temperature 9.8° C. The solution was saturated with ethylene by stirring vigorously under an ethylene atmosphere for 30 minutes. Approximately 10 mg AgOTf were then added to activate the catalyst. Vigorous stirring was continued under one bar ethylene; the polymerization reaction was allowed to proceed for 26 minutes. The reaction was then quenched by bubbling a vigorous stream of CO through the solution. An aliquot of the solution was filtered through a plug of glass-wool to remove silver-salts, diluted 50-fold with $CH_2Cl_2$ and analyzed by electrospray ionization mass spectrometry.

This invention has been illustrated for the screening of certain organometallic polymerization catalysts for the production of polyolefins. The invention is not, however, limited to the specifically exemplified catalysts or to the specifically exemplified polymerization reaction. Methods, techniques and instrumentation other than those specifically disclosed herein can be employed in the practice of this invention. A variety of mass spectrometric methods can be applied to achieve the ion-selection and daughter ion generation as described herein. In addition, a variety of methods for ionization and generation of daughter ions are known in the art and can be employed to achieve the results described herein.

All references cited herein are incorporated by reference herein in their entirety to the extent not inconsistent herewith.

Scheme I

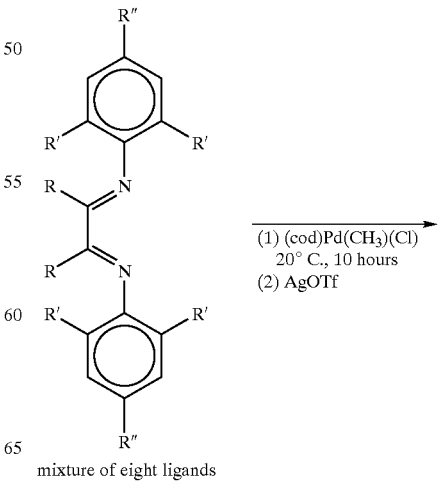

mixture of eight ligands

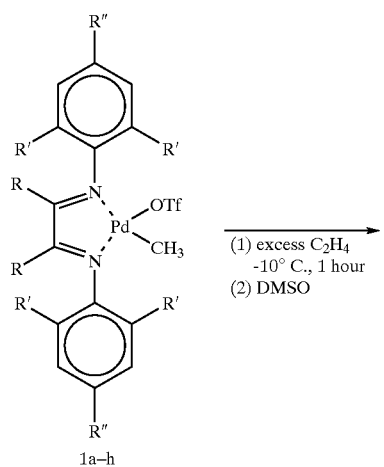
1a–h
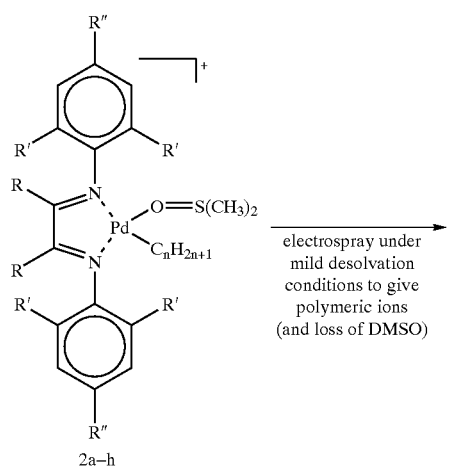
2a–h
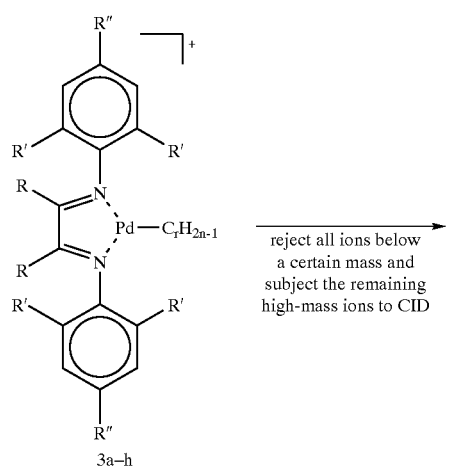
3a–h
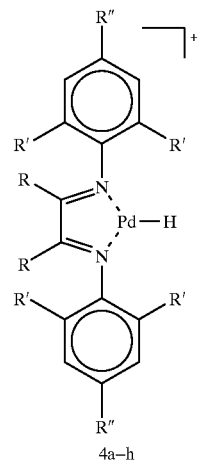
4a–h
|   | principal m/z for 4 a–h |
|---|---|
| (a) R = Me, R' = H, R" = H | 343 |
| (b) R = Me, R' = Me, R" = H | 399 |
| (c) R = Me, R' = iso-Pr, R" = H | 511 |
| (d) R = Me, R' = Me, R" = Me | 427 |
| (e) R = Me, R' = Me, R" = Br | 557 |
| (f) R = H, R' = Me, R" = H | 371 |
| (g) R = H, R' = iso-Pr, R" = H | 483 |
| (h) R = H, R' = Me, R" = Br | 529 |
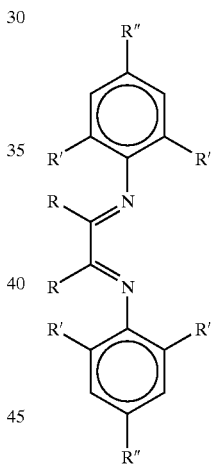
mixture of eight ligands
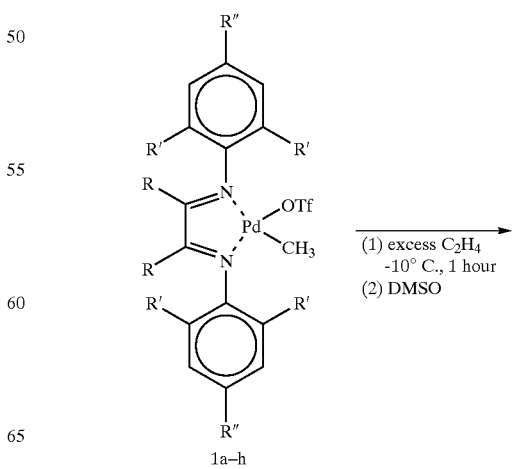
1a–h -continued

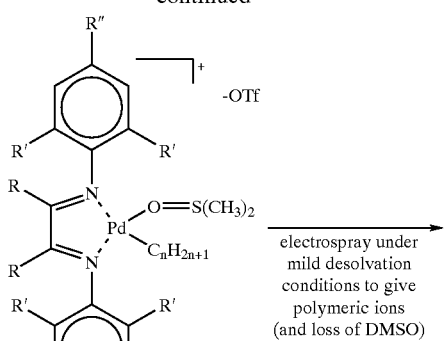

2a–h

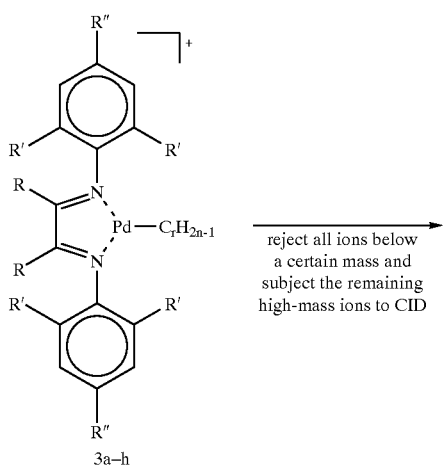

3a–h

| | principal m/z for 4 a–h |
|---|---|
| (a) R = Me, R' = H, R" = H | 343 |
| (b) R = Me, R' = Me, R" = H | 399 |
| (c) R = Me, R' = iso-Pr, R" = H | 511 |
| (d) R = Me, R' = Me, R" = Me | 427 |
| (e) R = Me, R' = Me, R" = Br | 557 |
| (f) R = H, R' = Me, R" = H | 371 |
| (g) R = H, R' = iso-Pr, R" = H | 483 |
| (h) R = H, R' = Me, R" = Br | 529 |

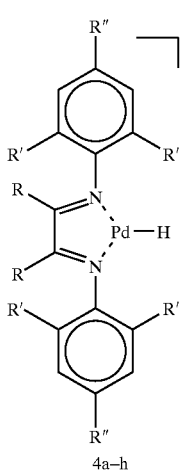

4a–h

Assay of Catalyst Performance going from Metal-bound Oligomers to Prediction of Bulk Polymer Properties Scheme 3

| | |
|---|---|
| Solvent: | $CH_2Cl_2$, 5 ml |
| Procatalyst: | (structure) 2 mg |
| Activation: | Addition of solid AgOTf to the thermostatted solution presaturated with ethylene under one bar ethylene pressure. |
| Temperature: | 9.8° C. |
| Reaction time: | 26 minutes |
| Quencher: | CO |
| Observed ion: | (structure) R = $CH_3$ (odd chains)<br>R = H (even chains) |
| Measurement time (on MS): | <5 minutes |

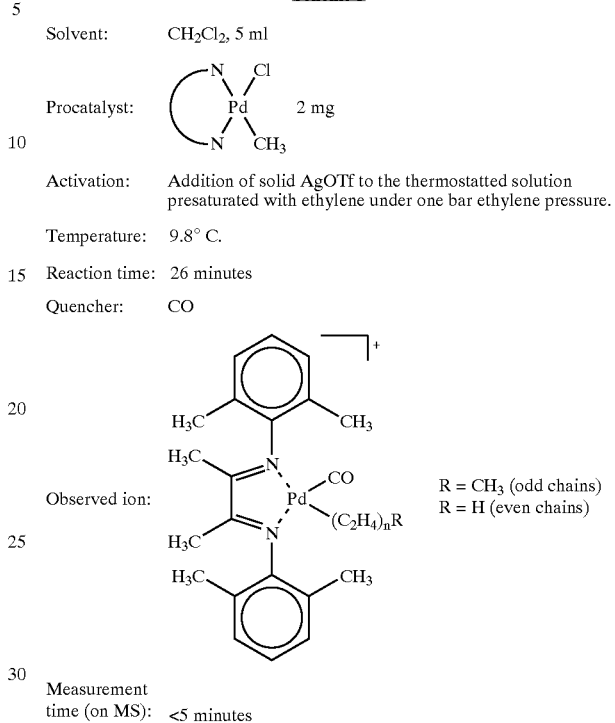

SCHEME 4

Kinetic scheme:

$k_{init}$

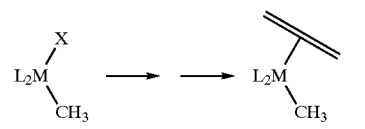

$k_{prop}$

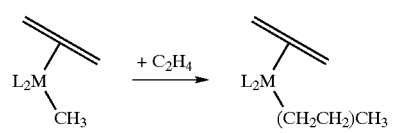

$k_{prop}$

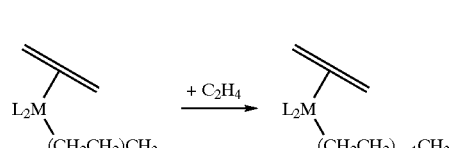

$k_{trans}$

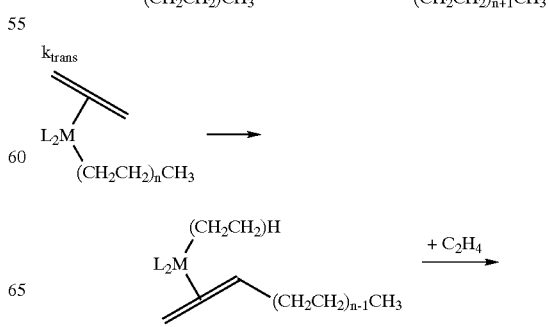

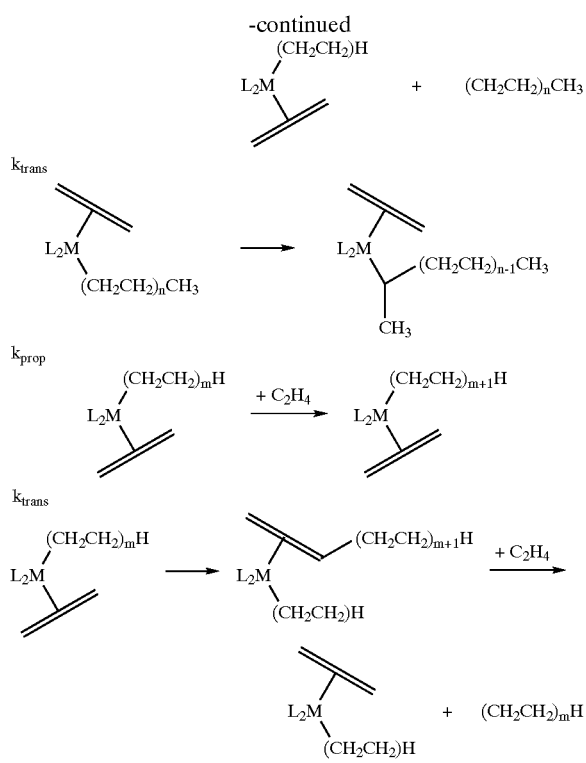

Assumptions:
(1) All rates are zero-order in olefin, i.e. coordination is fast and olefin is in excess*
(2) Propagation and chain-transfer rate constants are independent of chain length and structure.
(3) Chain-transfer and chain-branching occur through structurally similar transition states.**
(4) Release of the olefin-terminated polymer is pseudo-first order at high monomer concentration.
 *L.K. Johnson, C.M. Killan, M. Brookhart, J Am. Chem. Soc. 1995, 117, 6414
 **P. Margl, L. Deng. T. Ziegler, J. Am. Chem. Soc. 1999, 121, 154

We claim:

1. A method for identifying a compound that functions as a catalyst of a selected reaction which comprises the steps of:
   providing two or more compounds as test catalysts for a selected catalytic reaction;
   contacting the test catalysts with a selected reactant compound under conditions in which the selected catalytic reaction can occur to generate one or more reaction products from the reactant compound;
   quenching any catalytic reaction of the reactant compound; and
   analyzing reaction products of the quenched reaction by tandem mass spectrometric analysis to:
   a. select ions that are associated with one or more reaction products and in which the reaction product remains attached to a test catalyst or a portion thereof; and
   b. analyze the selected ions to determine which catalyst or catalysts generated the one or more reaction products
to thereby identify a compound that functions as a catalyst of the selected reaction.

2. The method of claim 1 wherein the ions associated with the selected reaction product are analyzed by use of an ion-molecule reaction.

3. The method of claim 1 wherein the analysis of products is performed by electrospray ionization tandem mass spectrometry.

4. The method of claim 3 wherein the selected reaction products are analyzed by collision-induced dissociation.

5. The method of claim 1 wherein the selected reaction is a polymerization reaction.

6. The method of claim 5 wherein the ions associated with the selected reaction product are analyzed by use of an ion-molecule reaction.

7. The method of claim 5 wherein the selected reaction is an olefin polymerization reaction.

8. The method of claim 5 wherein the test catalysts are organometallic complexes.

9. The method of claim 1 wherein reaction product ions are selected on the basis of mass.

10. The method of claim 1 wherein the selected reaction is a polymerization reaction and wherein the reaction product ions have m/z higher than a selected cut-off mass.

11. The method of claim 10 wherein the cut-off mass is m/z=1000.

12. The method of claim 1 wherein the selected reaction is olefin-CO copolymerization.

13. The method of claim 1 wherein the two or more test catalysts are simultaneously reacted with the selected reactant compound.

14. The method of claim 1 wherein ions associated with one or more reaction products and in which the reaction product remains attached to a test catalyst or a portion thereof that have m/z higher than a selected cut-off mass are selected and the mass selected ions are subjected to collision-induced dissociation to identify the test catalyst from which they derive.

15. A method for determining the ratio of propagation rate to chain transfer rate in a catalyzed polymerization reaction which comprises the steps of:
   reacting one or more test polymerization catalysts with a selected monomer under selected conditions to generate polymeric products;
   quenching the reaction; and
   analyzing the reaction products frm the quenched reaction using electrospray tandem mass spectrometry to measure the even-chainlodd-chain distribution to determine the ratio of propagation rate to chain transfer rates, wherein the catalyst is an organometallic complex and the even-chain/odd-chain distribution is measured by detecting the ratio of even-chain metal-bound polymeric ions to odd-chain metal-bound polymeric ions.

16. The method of claim 15 wherein two or more test polymerization catalysts are simultaneously reacted with the selected monomer.

17. A method for screening a library of test catalysts for catalytic activity which comprises the steps of:
   providing a library of test catalysts;
   contacting the test catalysts in the library with a selected reactant compound under conditions in which the selected catalytic activity can occur to generate reaction products from the reactant compound;
   quenching any catalytic reaction of the reactant compound; and
   analyzing reaction products from the quenched reaction by tandem mass spectrometric analysis to:
   a. select ions that are associated with one or more reaction products and in which the reaction product remains attached to a test catalyst or a portion thereof; and
   b. analyze the selected ions to determine which catalyst or catalysts generated the one or more reaction products
to determine which test catalyst in the library generated the selected reaction product to thereby determine catalytic activity of test catalysts in the library.

18. The method of claim 17 wherein the test catalysts are screened as polymerization catalysts.

19. The method of claim 17 wherein the test catalysts are organometallic complexes.

20. The method of claim 17 wherein the test catalysts are simultaneously reacted with the selected reactant compound.

21. The method of claim 17 wherein ions associated with one or more reaction products and in which the reaction product remains attached to a test catalyst or a portion thereof that have m/z higher than a selected cut-off mass are selected and the mass selected ions are subjected to collision-induced dissociation to identify the test catalyst from which they derive.

* * * * *